United States Patent [19]

Wegner et al.

[11] 4,412,959
[45] Nov. 1, 1983

[54] PROCESS FOR THE PRODUCTION OF MICROCAPSULES

[75] Inventors: Christian Wegner, Cologne; Gert Jabs, Odenthal; Manfred Dahm, Leverkusen, all of Fed. Rep. of Germany

[73] Assignee: Bayer Aktiengesellschaft, Leverkusen, Fed. Rep. of Germany

[21] Appl. No.: 271,607

[22] Filed: Jun. 8, 1981

[30] Foreign Application Priority Data

Jun. 14, 1980 [DE] Fed. Rep. of Germany ....... 3022453

[51] Int. Cl.$^3$ ............................................. B01J 13/02
[52] U.S. Cl. ....................................... 264/4.1; 8/526; 71/DIG. 1; 252/350; 252/364; 252/522 A; 252/604; 252/610; 428/320.6; 428/402.21; 428/914 502/9, 507
[58] Field of Search ...................... 252/316, 604, 610; 428/420, 320.6; 544/180, 298, 299; 8/526; 71/DIG. 1; 264/4

[56] References Cited

U.S. PATENT DOCUMENTS

| | | | |
|---|---|---|---|
| 1,911,689 | 5/1933 | Hentrich et al. | 544/180 X |
| 3,328,257 | 6/1967 | Vrancken et al. | 252/316 X |
| 3,432,327 | 3/1969 | Kan et al. | 427/150 X |
| 3,577,515 | 5/1971 | Vandegaer | 264/4 X |

*Primary Examiner*—Richard D. Lovering

*Attorney, Agent, or Firm*—Connolly and Hutz

[57] ABSTRACT

A process for the production of microcapsules by interfacial polyreaction, which comprises mixing a first reactant with an emulsion of a solution of a material to be encapsulated and a second reactant whereby the first and second reactants react to form a capsule containing the said material and wherein the second reactant dissolved in the disperse phase is a nitrogen-containing heterocyclic compound corresponding to one of the formulae I, II or III

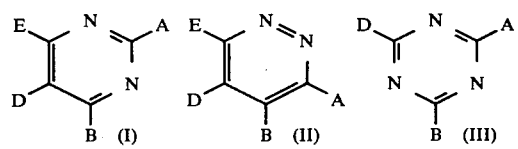

wherein at least two of the radicals A, B, D and E are halogen atoms, ammonium, hydrazinium, sulfonium, optionally substituted alkyl sulfonyl, aryl sulfonyl, aralkyl sulfonium, azido, aryloxy, thiocyano arylthio and sulfonic acid residues which are reactive under the conditions of the capsule-forming reaction and the remaining radicals A, B, D, E are hydrogen, alkyl, aryl, alkoxy, phenoxy, alkylamino or phenylamino radicals which are not reactive under the conditions of the capsule-forming reaction.

6 Claims, No Drawings

PROCESS FOR THE PRODUCTION OF MICROCAPSULES

This invention relates to the production of microcapsules using new wall-formers.

The microencapsulation of organic or inorganic materials is known in principle. One preferred process is the interfacial polyreaction in which two reactants are dissolved in immiscible liquids which then react with one another after combination in a high-turbulence zone to produce a polymer which forms the wall of the capsule (U.S. Nos. 3,575,882; 3,577,515 and 3,607,776).

In practice, microencapsulation by the interfacial reaction is carried out by initially preparing an emulsion in which the disperse phase consists of a solution of the material to be encapsulated in one (=the second) of the reactants required for the synthesis of the polymer. The continuous phase generally consists of water. The first, water-soluble reactant for the synthesis of the polymer is then added to the emulsion thus prepared. By the reaction of the two components, the polymer is formed at the phase interface of the dispersed spherical droplets and forms the shell of the microcapsule. Suitable reactants for the disperse phase are, for example, polyisocyanates, polycarbodiimides, polycarboxylic acid chlorides, polysulfonic acid chlorides, polychloroformic acid chlorides, phosgene and epoxides. The water-soluble reactant generally consists of compounds containing at least two OH-, NH- and/or SH-groups.

It has now been found that microcapsules can be obtained by the process described above providing the reactants used for the disperse phase for synthesising the walls of the microcapsules are nitrogen-containing, heterocyclic compounds corresponding to the following formulae:

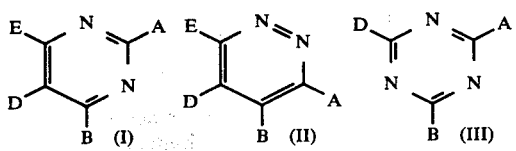

wherein at least 2 of the radicals A, B, D and E are halogen atoms (fluorine, chlorine and bromine), ammonium, hydrazinium, sulfonium, optionally substituted alkyl sulfonyl, aryl sulfonyl, aralkyl sulfonium, azido, aryloxy, thiocyano, arylthio and sulfonic acid residues which are reactive under the conditions of the capsule wall-forming reaction and the remaining radicals A, B, D, E are hydrogen, alkyl, aryl, alkoxy, phenoxy, alkylamino and phenylamino radicals which are not reactive under the conditions of the capsule wall-forming reaction.

Preferred reactive radicals are halogen, particularly fluorine and chlorine, and also methyl, ethyl and phenyl sulfonyl radicals.

Accordingly, the present invention provides a process for the production of microcapsules by interfacial polyreaction which is characterised in that the reactant dissolved in the disperse phase is a compound corresponding to the formulae I, II or III.

Examples of compounds corresponding to formulae I, II and III which may be used in accordance with the invention are 2,4,6-trichlorotriazine, 2,4,6-trifluorotriazine, tetrachloropyrimidine, 5-chloro-2,4,6-trifluoropyrimidine, 2-sulfonyl methyl-4-methyl-5,6-dichloropyrimidine, 2,6-difluoro-4-methyl-5-chloropyrimidine, tetrachloropyridazine, 2,4-dichloro-6-phenyl triazine, 2,4-dichloro-6-methyl triazine and 2,4-dichloro-6-(2-methoxy)-triazine. Mixtures of these compounds may also be used.

The capsules containing the wall-formers according to the invention may be produced by the known methods of interfacial polyreaction. Thus, a 3 to 30% and preferably a 7 to 20% solution of the wall-former according to the invention in the medium to be encapsulated is initially prepared. The resulting solution is then dispersed at room temperature in such a quantity of water that the concentration of the organic phase in the emulsion amounts to between 5 and 40% and preferably to between 15 and 35%. The size of the disperse droplets may be varied as required within limits of $3\mu$ to $500\mu$. It is advantageous to add protective colloids, such as polyvinyl alcohols for example, and/or emulsifiers to the aqueous solution before dispersion is carried out. When the required particle size has been reached, an at least difunctional, water-soluble component reactive with the compounds of formulae I, II or III is added to the dispersion at room temperature while agitating with a laboratory stirrer, the reactive component in question preferably being used in the form of a 20 to 80% aqueous solution. The dispersion is then stirred for from 30 minutes to 8 hours and preferably for 1 to 3 hours at room temperature and then for 30 minutes to 4 hours at temperatures in the range from 30° C. to 80° C. and preferably for 30 minutes to 2 hours at temperatures in the range from 45° C. to 65° C. Agglomerate-free, dense and stable microcapsule dispersions are obtained in this way.

Reactive components (chain-extending agents) which react with compounds corresponding to formulae I, II and III are preferably water-soluble aliphatic, cycloaliphatic, araliphatic or aromatic compounds which contain at least two Zerewitinoff-active hydrogen atoms, i.e. essentially OH-, NH- and/or SH-compounds.

Examples of such compounds are ethylene glycol, 1,2-propane diol and 1,3-propane diol, 1,4-butane diol, 1,3-butane diol, 1,6-hexane diol, trimethylol propane, glycerol, pentaerythritol, glucose, saccharose, ethanolamine, diethanolamine, triethanolamine, N-methyl ethanolamine, isopropanolamine, hydrazine, ethylene diamine, diethylene triamine, triethylene tetramine, hexamethylene diamine, isophorone diamine, 2,4- and 2,6-diaminotoluene.

Mixtures of the above-mentioned components and the polyethers obtainable therefrom by the addition of ethylene oxide or propylene oxide may also be used.

By virtue of their greater reactivity, preferred chain-extending agents are lower polyamines, particularly hydrazine, ethylene diamine, diethylene triamine, isophorone diamine and mixtures thereof. It is also possible to use chain-extending agents containing functional groups, for example, dimethylol propionic acid or the sodium salt of 2-(2-aminoethylamino)ethane sulfonic acid.

The relative quantities in which the compounds of formulae I, II or III and the chain-extending agents are used may be selected such that a molar ratio between the respective functional groups of from 1:0.8 to 1:2 and preferably about 1:1 is obtained.

In cases where chain-extending agents containing NH-groups and halogen-containing compounds of formulae I, II or III are used, the hydrohalic acid formed during the polyreaction consumes part of the chain-extending agent through salt formation. In this case, therefore, the amine has to be used in a 1.5 to 10 fold and preferably in a 2 to 4 fold excess.

There are no limitations so far as the component to be encapsulated is concerned providing it is liquid at room temperature and miscible with water and is capable of dissolving the wall-formers according to the invention in a concentration sufficient for wall-formation. The component to be encapsulated may also be a mixture of several substances. It is also possible to use solutions of one or more solids.

Examples of materials to be encapsulated are organic solvents, such as toluene or chloroform, plant-protection agents, oils, waxes, flameproofing agents, solutions of dyes and leuco dyes, perfume oils, adhesives, catalysts and blowing agents.

It is also possible to free the capsules from water by spray-drying in order to obtain a capsule powder. Alternatively, however, the dispersants may be exchanged to produce capsules which are dispersed in an organic medium as the outer phase.

EXAMPLE 1

Encapsulation of a solvent

A solution of 12 g of 2,4,6-trichlorotriazine in 138 g of dibutyl phthalate is emulsified in 300 g of a 0.5% aqueous solution of a polyvinyl alcohol (degree of hydrolysis 88%) using an ultrasonic pipe, a particle size of 9 μm being obtained. A solution of 18 g of diethylene triamine in 32 g of deionised water is then added with stirring using a laboratory stirrer. The dispersion is stirred for 1 hour at room temperature and then for 2 hours at 60° C. A dispersion is obtained which contains the solvent in round, agglomerate-free capsules. Encapsulation may also be successfully carried out with half the amount of amine.

EXAMPLE 2

Encapsulation of a solvent

A solution of 22.5 g of tetrachloropyrimidine in 127.5 g of diisopropyl naphthalene is emulsified in accordance with the procedure of Example 1. 15.6 g of diethylene triamine and 8.4 g of ethylene diamine dissolved in 20 g of water are then added. After stirring for 1 hour at room temperature and then for 2 hours at 50° C., an agglomerate-free capsule dispersion of a solvent is obtained.

EXAMPLE 3

Encapsulation of a flameproofing agent

A solution of 22.5 g of 5-chloro-2,4,6-trifluoropyrimidine in 127.5 g of trichloroethyl phosphate is emulsified in accordance with the procedure of Example 1. 15.6 g of diethylene triamine and 8.4 g of ethylene diamine dissolved in 26 g of water are then added. After stirring for 1 hour at room temperature and then for 2 hours at 50° C., a capsule dispersion of a flame-proofing agent is obtained.

EXAMPLE 4

Encapsulation of a leuco dye 11.2 g of a biuretised hexamethylene diisocyanate (NCO:21%) and 11.2 g of 2,4,6-trichlorotriazine are dissolved in 127.5 g of dibutyl phthalate containing 3% of paratoluene sulfinate of Michlers' hydrol and emulsified in accordance with Example 1. A solution of 16.3 g of diethylene triamine in 33.7 g of water is then added, followed by stirring for 1 hour at room temperature and then for 2 hours at 60° C. A dense, temperature-stable and agglomerate-free ink capsule dispersion is obtained which may be used for the production of carbonless copying papers.

EXAMPLE 5

Encapsulation of a plant protection agent 11.2 g of 2,4,6-trichlorotriazine and 11.2 g of a hexamethylene diisocyanate containing isocyanate groups (NCO:22%) are dissolved in 127.5 g of diethoxy thiophosphoryloximino-phenyl acetonitrile and the resulting solution is emulsified in 250 g of a 0.5% solution of a polyvinyl alcohol (degree of hydrolysis 88%) until the average particle size is 4 μm. 99.8 g of a 50% aqueous solution of the sodium salt of 2-(2-aminoethylamino)-ethane sulfonic acid are then added with stirring using a laboratory stirrer. After stirring for 1 hour at room temperature and then for 2 hours at 60° C., a readily redispersible capsule dispersion of a plant protection agent is obtained.

We claim:

1. A process for the production of microcapsules by interfacial polyreaction, which comprises mixing a first reactant with an emulsion of a solution of a material to be encapsulated and a second reactant whereby the first and second reactants react to form a capsule containing the said material and wherein the second reactant dissolved in the disperse phase is a nitrogen-containing heterocyclic compound corresponding to one of the formulae (I), (II) or (III):

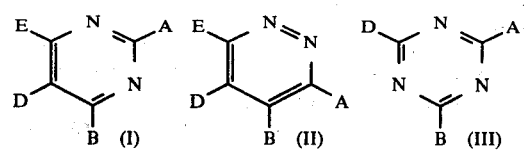

wherein at least two of the radicals A, B, D and E are halogen atoms, ammonium, hydrazinium, sulfonium, optionally substituted alkyl sulfonyl, aryl sulfonyl, aralkyl sulfonium, azido, aryloxy, thiocyano arylthio and sulfonic acid residues which are reactive under the conditions of the capsule-forming reaction and the remaining radicals A, B, D, E are hydrogen, alkyl, aryl, alkoxy, phenoxy, alkylamino or phenylamino radicals which are not reactive under the conditions of the capsule-forming reaction.

2. A process according to claim 1, wherein the first reactant is a water-soluble, aliphatic, cycloaliphatic, araliphatic or aromatic compound which contains at least two Zerewitinoff-active hydrogen atoms.

3. A process according to claim 1 or 2, wherein the molar ratio between the functional groups of the first and second reactants is from 1:0.8 to 1:2.

4. A process according to claim 1 or 2 wherein the first reactant contains one or more NH-groups and the second reactant contains one or more halogen atoms and wherein the first reactant is used in a 1.5 to 10 fold excess.

5. A process according to claim 1 or 2, wherein the reactive radicals of the compounds of formulae (I), (II) or (III) are selected from the group consisting of halogen atoms and methyl, ethyl, phenyl and sulfonyl radicals.

6. A process according to claim 1 or 2, wherein the material to be encapsulated is an organic solvent, plant-protection agent, oil, wax, flameproofing agent, solution of a dye, leuco dye, perfume oil, adhesive, catalyst or a blowing agent.

* * * * *